US011229592B2

(12) United States Patent
Paul et al.

(10) Patent No.: US 11,229,592 B2
(45) Date of Patent: *Jan. 25, 2022

(54) METHOD FOR HAIR VOLUME REDUCTION

(71) Applicant: Conopco, Inc., Englewood Cliffs, NJ (US)

(72) Inventors: Prem Kumar Cheyalazhagan Paul, Wirral (GB); Susan Pye, Wirral (GB); Charlotte Breony Tandy Rogers, Cheshire (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/756,325

(22) PCT Filed: Oct. 15, 2018

(86) PCT No.: PCT/EP2018/078118
§ 371 (c)(1),
(2) Date: Apr. 15, 2020

(87) PCT Pub. No.: WO2019/076835
PCT Pub. Date: Apr. 25, 2019

(65) Prior Publication Data
US 2020/0237633 A1     Jul. 30, 2020

(30) Foreign Application Priority Data

Oct. 20, 2017    (EP) .................................... 17197654

(51) Int. Cl.
*A61Q 5/06* (2006.01)
*A61K 8/44* (2006.01)

(52) U.S. Cl.
CPC . *A61K 8/44* (2013.01); *A61Q 5/06* (2013.01)

(58) Field of Classification Search
None
See application file for complete search history.

(56) References Cited

U.S. PATENT DOCUMENTS

2014/0301965 A1     9/2014   Schroeder et al.

FOREIGN PATENT DOCUMENTS

| JP | 2009007283 | 1/2009 | |
| JP | 2012172044 | 10/2012 | |
| WO | WO2008126030 | 10/2008 | |
| WO | WO-2008126030 A2 * | 10/2008 | ............... A61K 8/44 |
| WO | WO2013010991 | 1/2013 | |
| WO | WO201 3092209 | 6/2013 | |
| WO | WO2013087644 | 6/2013 | |
| WO | WO2015155047 | 10/2015 | |
| WO | WO2017096153 | 8/2017 | |

OTHER PUBLICATIONS

Search Report and Written Opinion in EP17197646; dated Dec. 1, 2017.
Search Report and Written Opinion in EP17197641; dated Dec. 22, 2017.
Search Report and Written Opinion in EP17197654; dated Jan. 17, 2018.
Search Report and Written Opinion in PCTEP2018076337; dated Oct. 25, 2018.
Search Report and Written Opinion in PCTEP2018076618; dated Nov. 15, 2018.
Written Opinion for PCTEP2018078118; dated Sep. 9, 2019.
Written Opinion IPEA PCTEP2018076618; dated Oct. 29, 2019.
IPRP2 in PCTEP2018076618; dated Feb. 11, 2020.
IPRP2 in PCTEP2018078118; dated Feb. 5, 2020.

* cited by examiner

*Primary Examiner* — Melissa S Mercier
(74) *Attorney, Agent, or Firm* — Edward A. Squillante, Jr.

(57) ABSTRACT

The present invention is in the field of hair treatment compositions; in particular relates to a method for hair volume reduction. Despite the prior art, there still exists the opportunity to increase the conditioning benefits delivered through hair treatment compositions. It is therefore an object of the present invention to provide a method that retains shape and reduces frizz even after exposure to humidity and washing the hair. It has been found that reduced hair frizz and hair shape retention even after exposure to moisture can be obtained by using N-formyl amino acids.

17 Claims, No Drawings

METHOD FOR HAIR VOLUME REDUCTION

CROSS REFERENCE TO RELATED APPLICATION

This application is a U.S. National Stage Application under 35 U.S.C. § 371 of International Application No. PCT/EP2018/078118, filed on Oct. 15, 2018, which claims the benefit of European Application No. 17197654.1, filed on Oct. 20, 2017, the entire disclosures of which are hereby incorporated by reference for any and all purposes.

FIELD OF THE INVENTION

The present invention is in the field of hair treatment compositions; in particular relates to a method for hair volume reduction.

BACKGROUND OF THE INVENTION

Frizz is generally known as hair that does not align with the surrounding hairs, but stands up or curls independently, creating a fuzzy or irregular texture thereby giving voluminous or bushy look to the hair. Generally, hair gets frizzy on days when there is humid weather and the level of moisture in the air is high. As a result, hair appears dry and frizzy instead of smooth, shiny and defined. The appearance of frizz and loss of shine and smoothness are associated with a perception of poor hair health.

A common method of providing conditioning benefits to the hair is through the use of conditioning agents such as cationic surfactants and polymers, high melting point fatty compounds, low melting point oils, silicone compounds, and mixtures thereof. Deposition of these materials onto the hair surface results in hair having a greasy feel and look which is undesired.

US 2016/0158128 discloses a rinse-off conditioner composition for hair frizz reduction comprising from about 0.2% to about 20% of a moisture control material or mixture of moisture control materials.

Despite the prior art, there still exists the opportunity to increase the conditioning benefits delivered through hair treatment compositions.

It is therefore an object of the present invention to provide a method for frizz reduction.

It is another object of the present invention to provide a method that retains shape and reduces frizz even after exposure to humidity.

It is yet another object of the present invention to a provide a method with hair shape benefits and frizz reduction even after washing the hair.

Surprisingly, it has been found that reduced hair frizz and hair shape retention even after exposure to moisture can be obtained by using N-formyl amino acids.

SUMMARY OF THE INVENTION

Accordingly, in a first aspect, the present invention provides a method for reducing hair volume, the method comprising the step of treating the hair with an aqueous treatment composition comprising an aqueous phase comprising at least 0.5% by weight of N-formyl amino acid.

In the context of the present invention, the reference to "hair" typically means mammalian hair including scalp hair, facial hair and body hair, more preferably hair on the human head and scalp.

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

DETAILED DESCRIPTION OF THE INVENTION

In a first aspect, the present invention relates to a method for hair volume reduction comprising treating the hair with an aqueous treatment composition comprising an aqueous phase comprising N-formyl amino acid.

By "aqueous phase" is meant a phase which has water as its basis. Accordingly, the aqueous treatment composition will generally comprise at least 60%, preferably at least 65% and more preferably at least 70%, still more preferably at least 75%, even more preferably at least 80% or even at least 90% water by weight of the total composition. Preferably, the composition comprises no more than 99.5% and more preferably no more than 98% water by weight of the total composition. Other organic solvents may also be present, such as lower alkyl alcohols and polyhydric alcohols. Examples of lower alkyl alcohols include $C_1$ to $C_6$ monohydric alcohols such as ethanol and isopropanol. Examples of polyhydric alcohols include propylene glycol, hexylene glycol, glycerin, and propanediol. Mixtures of any of the above described organic solvents may also be used.

Preferably the aqueous phase is an aqueous continuous phase. By "aqueous continuous phase" is meant a continuous phase which has water as its basis.

The aqueous treatment composition of the present invention comprises at least 0.5% N-formyl amino acid by weight of the total composition.

Suitable N-formyl amino acids include N-formyl standard amino acids and their derivatives. Typical examples are N-formyl alanine, N-formyl proline, N-formyl methionine, N-formyl valine, N-formyl leucine and N-formyl glycine. The most preferred N-formyl amino acid is N-formyl glycine.

The N-formyl amino acids may be used in the free acid form or in the form of salts such as the sodium, potassium, and ammonium salts, or the lower alkanolamine salts (such as mono-, di- and triethanolamine salts and mono-, di- and triisopropanolamine salts). Mixtures of any of the above-described forms may also be suitable.

Preferably the N-formyl amino acids is used in the free acid form, and at a level ranging from 0.5 to 6%, more preferably from 1 to 3% and most preferably from 1.5 to 2.5% by weight of the total composition.

Shampoo Compositions

A particularly preferred aqueous treatment composition for use in the method in accordance with the invention is a shampoo composition.

Such a shampoo composition will comprise one or more cleansing surfactants which are cosmetically acceptable and suitable for topical application to the hair. Further surfactants may be present as an additional ingredient if sufficient for cleansing purposes is not provided as emulsifier for the silicone component. It is preferred that shampoo compositions of the invention comprise at least one further surfactant (in addition to that used as emulsifying agent for the silicone component) to provide a cleansing benefit.

Suitable cleansing surfactants, which may be used singularly or in combination, are selected from anionic, amphoteric and zwitterionic surfactants, and mixtures thereof. The cleansing surfactant may be the same surfactant as the emulsifier, or may be different.

Shampoo compositions according to the invention will typically comprise one or more anionic cleansing surfactants which are cosmetically acceptable and suitable for topical application to the hair.

Examples of suitable anionic cleansing surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic cleansing surfactants for use in shampoo compositions of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, sodium lauryl ether sulphate(n)EO, (where n ranges from 1 to 3), ammonium lauryl sulphate and ammonium lauryl ether sulphate(n)EO, (where n ranges from 1 to 3).

Mixtures of any of the foregoing anionic cleansing surfactants may also be suitable.

The total amount of anionic cleansing surfactant in shampoo compositions of the invention is generally from 5 to 30, preferably from 6 to 20, more preferably from 8 to 16 wt %.

The shampoo composition can optionally include co-surfactants, to help impart aesthetic, physical or cleansing properties to the composition.

A preferred example is an amphoteric or zwitterionic surfactant, which can be included in an amount ranging from 0 to about 8, preferably from 1 to 4 wt %.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

Another preferred example is a nonionic surfactant, which can be included in an amount ranging from 0 to 8, preferably from 2 to 5 wt %.

For example, representative nonionic surfactants that can be included in shampoo compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Other sugar-derived nonionic surfactants which can be included in shampoo compositions of the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92 06154 and U.S. Pat. No. 5,194,639, and the N-alkoxy polyhydroxy fatty acid amides, such as $C_{10}$-$C_{18}$ N-(3-methoxypropyl) glucamide.

The shampoo composition may also optionally include one or more cationic co-surfactants included in an amount ranging from 0.01 to 10, more preferably from 0.05 to 5, most preferably from 0.05 to 2 wt %.

The total amount of surfactant (including any co-surfactant, and/or any emulsifier for the silicone component) in shampoo compositions of the invention is generally from 0.1 to 50, preferably from 5 to 30, more preferably from 10 to 25 wt %.

Conditioner

An aqueous treatment composition for use in the method in accordance with the invention may also be formulated as conditioners for the treatment of hair (typically after shampooing) and subsequent rinsing.

The aqueous treatment composition of the present invention may suitably include a conditioning gel phase, which may be generally characterized as a gel (Lβ) surfactant mesophase consisting of surfactant bilayers. Such a conditioning gel phase may be formed from a cationic surfactant, a high melting point fatty alcohol and an aqueous carrier. Typically, these components are heated to form a mixture, which is cooled under shear to room temperature. The mixture undergoes a number of phase transitions during cooling, normally resulting in a gel (Lβ) surfactant mesophase consisting of surfactant bilayers.

Examples of suitable cationic surfactants which are useful for forming the conditioning gel phase include quaternary ammonium cationic surfactants corresponding to the following general formula:

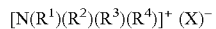

$$[N(R^1)(R^2)(R^3)(R^4)]^+ \ (X)^-$$

in which $R^1$, $R^2$, $R^3$, and $R^4$ are each independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halide, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated. Specific examples of such quaternary ammonium cationic surfactants of the above general formula are cetyltrimethylammonium chloride, behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, dipalmitoylethyldimethylammonium chloride, PEG-2 oleylammonium chloride and salts of these, where the chloride is replaced by other halide (e.g., bromide), acetate, citrate, lactate, glycolate, phosphate nitrate, sulphate, or alkylsulphate.

In a preferred class of cationic surfactant of the above general formula, $R^1$ is a $C_{16}$ to $C_{22}$ saturated or unsaturated, preferably saturated, alkyl chain and $R^2$, $R^3$ and $R^4$ are each independently selected from $CH_3$ and $CH_2CH_2OH$, preferably $CH_3$. Specific examples of such preferred quaternary ammonium cationic surfactants for use in forming the conditioning gel phase are cetyltrimethylammonium chloride (CTAC), behenyltrimethylammonium chloride (BTAC) and mixtures thereof.

Mixtures of any of the above-described cationic surfactants may also be suitable.

The level of cationic surfactant suitably ranges from 0.1 to 10%, preferably from 0.2 to 5% and more preferably from 0.25 to 4% (by weight based on the total weight of the composition).

By "high melting point" in the context of this invention is generally meant a melting point of 25° C. or higher. Generally, the melting point ranges from 25° C. up to 90° C., preferably from 40° C. up to 70° C. and more preferably from 50° C. up to about 65° C.

The high melting point fatty alcohol can be used as a single compound or as a blend or mixture of at least two high melting point fatty alcohols. When a blend or mixture of fatty alcohols is used, the melting point means the melting point of the blend or mixture.

Suitable fatty alcohols of this type have the general formula R—OH, where R is an aliphatic carbon chain. Preferably R is a saturated aliphatic carbon chain comprising from 8 to 30 carbon atoms, more preferably from 14 to 30 carbon atoms and most preferably from 16 to 22 carbon atoms.

R can contain, in addition to carbon and hydrogen atoms, ether linkages, and other groups such as amino groups.

Most preferably, the fatty alcohol has the general formula $CH_3(CH_2)_nOH$, where n is an integer from 7 to 29, preferably from 15 to 21.

Specific examples of suitable fatty alcohols are cetyl alcohol, stearyl alcohol, behenyl alcohol, and mixtures thereof. Cetyl alcohol, stearyl alcohol and mixtures thereof are particularly preferred.

Mixtures of any of the above-described fatty alcohols may also be suitable.

The level of fatty alcohol suitably ranges from 0.01 to 10%, preferably from 0.1 to 8%, more preferably from 0.2 to 7% and most preferably from 0.3 to 6% (by weight based on the total weight of the composition).

The weight ratio of cationic surfactant to fatty alcohol is suitably from 1:1 to 1:10, preferably from 1:1.5 to 1:8, optimally from 1:2 to 1:5.

Styling Compositions

An aqueous treatment composition for use in the method in accordance with the invention may also take the form of styling compositions.

Preferred product forms are leave on formulations such as gels, waxes and creams.

Alternative styling forms include mousses, sprays and aerosols.

Such styling products frequently include a carrier and further additional components. The carriers and additional components required to formulate such products vary with product type and can be routinely chosen by one skilled in the art. The following is a description of some of these carriers and additional components.

Hair care compositions of the present invention can comprise a carrier, or a mixture of such carriers, which are suitable for application to the hair. The carriers are present at from about 0.5% to about 99.5%, preferably from about 5.0% to about 99.5%, more preferably from about 10.0% to about 98.0%, of the composition. As used herein, the phrase "suitable for application to hair" means that the carrier does not damage or negatively affect the aesthetics of hair or cause irritation to the underlying skin.

Compositions according to the invention comprise a buffer or pH adjuster. Preferred buffers or pH adjusters include weak acids and bases such glycine/sodium hydroxide, citric acid, lactic acid, succinic acid, acetic salt and salts thereof. Frequently a mixture of buffering system is used such as sodium citrate and citric acid.

Carriers suitable for use with hair care compositions of the present invention include, for example, those used in the formulation of hair sprays, mousses, tonics, waters, creams gels, shampoos, conditioners, and rinses. The choice of appropriate carrier will depend on the particular product to be formulated. The carriers used herein can include a wide range of components conventionally used in hair care compositions. The carriers can contain a solvent to dissolve or disperse the styling compound being used, with water, the $C_1$-$C_6$ alcohols, lower alkyl acetate and mixtures thereof being preferred. The carriers can also contain a wide variety of additional materials such as acetone, hydrocarbons (such as isobutane, hexane, decene), halogenated hydrocarbons (such as Freons) and volatile silicones such as cyclomethicone.

When the hair care composition is a hair spray, tonic, gel, or mousse the preferred solvents include water, ethanol, volatile silicone derivatives, and mixtures thereof. The solvents used in such mixtures may be miscible or immiscible with each other. Mousses and aerosol hair sprays can also utilise any of the conventional propellants to deliver the material as a foam (in the case of a mousse) or as a fine, uniform spray (in the case of an aerosol hair spray). Examples of suitable propellants include materials such as trichlorofluoromethane, dichlorodifluoromethane, difluoroethane, dimethylether, propane, n-butane or isobutane. A tonic or hair spray product having a low viscosity may also utilise an emulsifying agent. Examples of suitable emulsifying agents include nonionic, cationic, anionic surfactants, or mixtures thereof. If such an emulsifying agent is used, it is preferably present at a level of from about 0.01% to about 7.5% by weight based on total weight of the composition. The level of propellant can be adjusted as desired but is generally from about 3% to about 30% by weight based on total weight for mousse compositions and from about 15% to about 50% by weight based on total weight for aerosol hair spray compositions.

Hair styling waxes, creams or gels also typically contain a structurant or thickener, typically in an amount of from 0.01% to 10% by weight.

Suitable spray containers are well known in the art and include conventional, non-aerosol pump sprays i.e., "atomisers", aerosol containers or cans having propellant, as described above, and also pump aerosol containers utilising compressed air as the propellant.

Aqueous treatment composition of the present invention may also incorporate other optional ingredients to enhance performance and/or consumer acceptability. Suitable optional ingredients include: preservatives, colouring agents, chelating agents, antioxidants, fragrances, antimicrobials, antidandruff agents, cationic conditioning polymers, sunscreens, proteins and hydrolysed proteins.

The aqueous treatment compositions of the present invention may also contain adjuncts suitable for hair care. Generally, such ingredients are included individually at a level of up to 2, preferably up to 1 wt % of the total composition. Suitable hair care adjuncts, include amino acids, sugars and ceramides.

An aqueous treatment composition for use in the method of the invention may also incorporate other optional ingredients to enhance performance and/or consumer acceptability. Suitable optional ingredients include: preservatives, colouring agents, chelating agents, antioxidants, fragrances, antimicrobials, antidandruff agents, cationic conditioning polymers, styling ingredients, sunscreens, proteins and hydrolysed proteins.

In the method of the invention, prior to treating the hair with the aqueous treatment composition, the hair may be washed with water alone or with shampoo.

In the method of the invention, the washed hair is soaked in the aqueous treatment composition. Generally, any application amount of aqueous treatment composition that covers the hair to be treated suffices. Lesser amounts may be used, for example, if only a section of hair or just the hair tips are to be treated. The aqueous treatment composition is preferably uniformly delivered, for example by working it from the root end to the tip end of the hair.

Preferably, the hair is soaked in the aqueous treatment composition for a period ranging from 1 to 60 minutes, more preferably from 3 to 45 minutes. At the end of the soaking period, it is preferred that the hair is dried or allowed to dry without rinsing the aqueous treatment composition from the hair. The soaked hair may be dried naturally by exposure to air, by use of a heated hair drying appliance, by rubbing with a water-absorbent article, or by a combination of any of these methods.

The aqueous treatment composition may thus remain in contact with the hair after initial application for a period of at least 1 minute, and preferably up until the next wash, e.g. 24 to 72 hours after initial application.

The invention is further illustrated with reference to the following, non-limiting Examples.

EXAMPLES

Example 1

Effect of N-Formyl Glycine on Hair

Dark brown European wavy hair switches of length 25 cm and weight 2 gms, were treated as follows:

Control: After initial washing, soaked for 30 minutes in water

Comparative Example A: After initial washing, soaked for 30 minutes in aqueous solution of 1% glycine Example 1: soaked for 30 minutes in aqueous solution of 1% N-formyl glycine At the end of the soaking period, the switches were left to dry at 20° C. and 50% RH. When dried, the switches were straightened with 5 passes of FHI irons (FHI Brands, 29003 Avenue Sherman Valencia, Calif. 91355 USA). The switches were then placed in a humidity chamber ~30 C/80% RH for 1 hour and images were captured and analyzed. The percentage benefit of the volume compared to their respective water controls are given in Table 1.

TABLE 1

| Treatment | After 1 hour at high humidity (30 C./80% RH) % shape and frizz control benefit against control |
| --- | --- |
| Comparative Example A | −6 |
| Example 1 | 30 |

It can be seen from the above table that hair switches treated with N-formyl glycine retains shape and controls frizz even after exposure to high humidity. Glycine on the other hand are no better than their control.

Example 2

Effect of N-Formyl Glycine on Hair for Long Lasting and Durable Volume Reduction The switches from the above example were subsequently washed and the images were captured. It was found that compared to control, N-formyl glycine treated switches maintained a 32% benefit over control showing the long lasting and durable benefit to provide volume reduction. The corresponding benefits for glycine was only −10%.

The invention claimed is:
1. A method for reducing hair volume, the method comprising the steps of: a) treating the hair with an aqueous treatment composition comprising an aqueous continuous phase, wherein the aqueous continuous phase comprises at least 1% by weight of N-formyl amino acid based on total weight of the aqueous treatment composition, and b) allowing the aqueous treatment composition to contact the hair for 1 to 60 minutes before the hair is dried further wherein the hair is hair on the head, the composition having N-formyl amino acid in free acid form, salt form or a mixture thereof.

2. The method according to claim 1 wherein the aqueous treatment composition comprises at least 60% by weight of water.

3. The method according to claim 1, wherein the N-formyl amino acid is N-formyl glycine.

4. The method according to claim 1, wherein the aqueous phase comprises 1% to 6% by weight of N-formyl amino acid based on total weight of the aqueous treatment composition.

5. The method according to claim 1, wherein the aqueous continuous phase comprises 60% to 98% by weight of water based on total weight of the aqueous treatment composition.

6. The method according to claim 1, wherein the aqueous continuous phase comprises at least 65% by weight water based on total weight of the aqueous treatment composition.

7. The method according to claim 1, wherein the hair is treated by soaking the hair in the aqueous treatment composition for a period ranging from 3 to 45 minutes.

8. The method according to claim 7, wherein after soaking the hair, the hair is dried by exposure to air, with a hair drying appliance, by rubbing the hair with a water-absorbent article or a combination thereof without rinsing the aqueous treatment composition from the hair.

9. The method according to claim 1, wherein after treating the hair with the aqueous treatment composition, the hair is dried by exposure to air, with a hair drying appliance, by rubbing the hair with a water-absorbent article or a combination thereof without rinsing the aqueous treatment composition from the hair.

10. The method according to claim 1, wherein the aqueous treatment composition is not removed from the hair and remains in contact with the hair for 24 to 72 hours after the hair is dried.

11. The method according to claim 1, wherein the method further results in hair shape retention.

12. The method according to claim 1, wherein the method further results in hair frizz reduction.

13. The method according to claim 1, wherein the aqueous treatment composition is a wax, cream, gel, spray, tonic, mousse, or conditioner.

14. The method according to claim 1, wherein the aqueous treatment composition further comprises a styling ingredient, antidandruff agent, antimicrobial agent, conditioning polymer or a sunscreen.

15. The method according to claim 1, wherein the aqueous treatment composition further comprises a surfactant.

16. The method according to claim 1, wherein the aqueous treatment composition comprises from 1 to 3% by weight N-formyl amino acid based on total weight of the aqueous treatment composition.

17. The method according to claim 1, wherein the aqueous treatment composition comprises from 1.5 to 2.5% by weight N-formyl amino acid based on total weight of the aqueous treatment composition.

* * * * *